United States Patent [19]

Wovcha et al.

[11] 4,293,645

[45] Oct. 6, 1981

[54] PROCESS FOR PREPARING ANDROSTA-1,4-DIENE-3,17-DIONE AND ANDROST-4-ENE-3,17-DIONE

[75] Inventors: Merle G. Wovcha; Candice B. Biggs, both of Kalamazoo; Thomas R. Pyke, Portage, all of Mich.

[73] Assignee: The Upjohn Company, Kalamazoo, Mich.

[21] Appl. No.: 849,526

[22] Filed: Nov. 9, 1977

Related U.S. Application Data

[63] Continuation-in-part of Ser. No. 662,563, Mar. 1, 1976.

[51] Int. Cl.³ .................................................. C12P 33/16
[52] U.S. Cl. ........................................ 435/55; 435/172; 435/865
[58] Field of Search ................................................ 435/55

[56] References Cited

U.S. PATENT DOCUMENTS

| | | | |
|---|---|---|---|
| 2,602,769 | 7/1952 | Murray et al. | 435/56 |
| 3,388,042 | 6/1968 | Arima et al. | 435/55 |
| 3,507,749 | 4/1970 | Sih | 435/55 |
| 3,684,657 | 8/1972 | Kraychy et al. | 435/55 |
| 3,759,791 | 9/1973 | Marsheck et al. | 435/55 |
| 4,035,236 | 7/1977 | Wovcha | 435/55 |

OTHER PUBLICATIONS

Mamoli et al., Ber. 70, 470 & 2079 (1937).

*Primary Examiner*—Alvin E. Tanenholtz
*Attorney, Agent, or Firm*—Roman Saliwanchik

[57] ABSTRACT

Mutants which are used in a novel microbiological process to selectively degrade steroids having 17-alkyl side chains of from 2 to 10 carbon atoms, inclusive, to androsta-1,4-diene-3,17-dione (ADD) and androst-4-ene-3,17-dione (AD). ADD and AD are valuable intermediates to make useful steroids.

8 Claims, No Drawings

PROCESS FOR PREPARING ANDROSTA-1,4-DIENE-3,17-DIONE AND ANDROST-4-ENE-3,17-DIONE

CROSS REFERENCE TO RELATED APPLICATION

This application is a continuation-in-part of our pending application Ser. No. 662,563, filed in The U.S. Patent and Trademark Office on Mar. 1, 1976.

BACKGROUND OF THE INVENTION

The transformation of steriods by microorganisms has been widely studied and documented. Apparently, the earliest such work was by Mamoli and Vercellone in 1937, Ber. 70, 470 and Ber. 70, 2079. They disclosed the reduction of 17-ketosteroids to 17β-hydroxysteroids by fermenting yeast. Since then, Peterson and Murray disclosed the 11α-hydroxylation of progesterone with the fungus *Rhizopus nigricans*; see, U.S. Pat. No. 2,602,769 (1952). More recently, Kraychy et al. in U.S. Pat. No. 3,684,657 (1972) discloses the selective microbiological degradation of steroidal 17-alkyls by fermenting a steroid containing at least 8 carbons in the 17-alkyl side chain with Mycobacterium sp. NRRL B-3683 to prepare androst-4-ene-3,17-dione, androst-1,4-diene-3,17-dione, and 20α-hydroxymethyl-pregna-1,4-dien-3-one. Even more recently, Marsheck et al. in U.S. Pat. No. 3,759,791 (1973) disclose the selective microbiological preparation of androst-4-ene-3,17-dione by fermenting a steroid of the cholestane or stigmastane series containing at least 8 carbons in the 17-alkyl side chain with Mycobacterium sp. NRRL B-3805.

BRIEF SUMMARY OF THE INVENTION

Mutants which are characterized by their ability to selectively degrade steroids having 17-alkyl side chains of from 2 to 10 carbon atoms, inclusive, and accumulate androsta-1,4-diene-3,17-dione, hereinafter referred to as ADD, and androst-4-ene-3,17-dione, hereinafter referred to as AD, in the fermentation beer. These mutants can be obtained from microorganisms of the following genera by using the mutation procedures disclosed herein or other mutation procedures: Arthrobacter, Bacillus, Brevibacterium, Corynebacterium, Microbacterium, Mycobacterium, Nocardia, Protaminobacter, Serratia, and Streptomyces. A preferred genus is Mycobacterium. Exemplary species of this genus are *M. phlei, M. smegmatis, M. rhodochrous, M. mucosum, M. fortuitum,* and *M. butyricum*. Specifically exemplified herein are the novel mutant microorganisms, *Mycobacterium fortuitum*, NRRL B-8153, and *Mycobacterium phlei*, NRRL B-8154, which are used to selectively degrade steroids having 17-alkyl chains of from 2 to 10 carbon atoms, inclusive, to ADD and AD. Examples of suitable steroid substrates are sitosterols, cholesterol, stigmasterol, campesterol, and like steroids with 17-alkyl side chains of from 2 to 10 carbon atoms, inclusive. These steroid substrates can be in either the pure or crude form.

DETAILED DESCRIPTION OF THE INVENTION

The Microorganisms

Mutants which are characterized by their ability to selectively degrade steroids having 17-alkyl side chains of from 2 to 10 carbon atoms, inclusive, and accumulate ADD and AD in the fermentation beer can be obtained by mutating microorganisms of the following genera: Arthrobacter, Bacillus, Brevibacterium, Corynebacterium, Microbacterium, Mycobacterium, Nocardia, Protaminobacter, Serratia, and Streptomyces. *Mycobacterium fortuitum*, ATCC 6842, and *Mycobacterium phlei*, UC 3533, have been mutated, as disclosed herein, to give novel laboratory mutant microorganisms.

The 1974 ATCC Catalogue discloses the following alongside the listing of ATCC 6842: "J. C. Cruz 2. Cold abscess. Acta Med. Rio de Janeiro 1:1 (1936). Medium 90 37C." *M. fortuitum*, ATCC 6842, degrades sterols non-selectively to small molecular weight compounds, e.g. $CO_2 + H_2O$. Thus, this microorganism is not suitable as a selective steroid degrader.

Mutation of *M. fortuitum*, ATCC 6842, and *M. phlei*, UC 3533 (UC denotes The Upjohn Company Culture Collection), using nitrosoguanidine has resulted in the production of novel mutants which selectively degrade steroids having 17-alkyl side chains of from 2 to 10 carbon atoms, inclusive, to produce ADD and AD. These mutant microorganisms have been given the accession numbers NRRL B-8153 and NRRL B-8154, respectively, by the Northern Regional Research Laboratory, U.S. Department of Agriculture, Peoria, Ill., U.S., where they have been deposited in the permanent collection. A subculture of these microorganisms is freely available from this depository by request made thereto. It should be understood that the availability of the cultures does not constitute a license to practice the subject invention in derogation of patent rights granted with the subject instrument by governmental action.

The microorganisms of the subject invention have been distinguished from the Mycobacterium species NRRL B-3805, disclosed in U.S. Pat. No. 3,759,791, which is discussed supra. NRRL B-3805 has the general characteristics of *Mycobacterium vaccae* which is a distinctly different species than the *M. fortuitum* and *M. phlei* of the subject invention. See Bergey's Manual of Determinative Bacteriology, 8th Edition, The Williams and Wilkins Company, 1974, on pages 695 and 696 for a comparison of these microorganisms.

The morphology and drug sensitivities of *M. fortuitum* NRRL B-8153 and *M. phlei* NRRL B-8154, are indistinguishable from that of the parent *M. fortuitum*, ATCC 6842, and *M. phlei*, UC 3533, respectively. Both *M. fortuitum* and *M. phlei* cultures are acid-fast monmotile, non-spore-forming bacilli belonging to the family Mycobacteriaceae of the order Actinomycetales. According to Runyons classification, Runyon, E. H. 1959 Med. Clin. North America 43: 273, *M. fortuitum* is a nonchromogenic group IV mycobacterium, i.e., it grows rapidly at low temperatures to produce nonpigmented colonies on relatively simple media. *M. phlei* is also a group IV mycobacterium but produces colonies which are deep yellow to orange when grown on simple media.

*M. fortuitum* ATCC 6842 and *M. fortuitum* NRRL B-8153, are clearly distinguishable in their action on steroid molecules. As disclosed above, *M. fortuitum* ATCC 6842 is a non-selective degrader of steroids, whereas *M. fortuitum* NRRL B-8153 is a selective degrader. This property of *M. fortuitum* NRRL B-8153 makes it highly useful, as disclosed herein. Further, *M. phlei* UC 3533 and *M. phlei* NRRL B-8154 are also distinguishable in their action on steroid molecules. *M. phlei* UC 3533 is a non-selective degrader, whereas NRRL B-8154 is a selective degrader.

The mutation of *M. fortuitum* ATCC 6842 and *M. phlei* UC 3533 to give *M. fortuitum* NRRL B-8153 and *M. phlei* NRRL B-8154, respectively, was accomplished by the use of nitrosoguanidine. The details of the procedure are described infra. Though mutation procedures are generally known in the art, there is no known art which teaches or even suggests the type of mutants, if any, which might be obtained by use of the subject mutation procedure. Also, though the mutation and transformation procedures, disclosed herein, are detailed for a Mycobacterium, it should be understood that similar or equivalent procedures can be used with microorganisms of the other genera, as disclosed herein.

The Transformation Process

The selective transformation of the subject invention can be effected in a growing culture of *M. fortuitum* NRRL B-8153 or *M. phlei* NRRL B-8154 by either adding the selected steroid substrate to the culture during the incubation period, or incorporating it in the nutrient medium prior to inoculation. The steroid can be added singly or in combination with another steroid. The preferred, but not limiting, range of concentration of the steroid in the culture is about 0.1 to about 100 grams per liter. The culture is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, ammonium salts and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

The transformation process can range from about 72 hours to 15 days or more. The incubation temperature can range from about 25° C. to about 37° C., with 30° C. being preferred for NRRL B-8153 and 35° C. for NRRL B-8154. The contents are aerated with sterilized air and agitated to facilitate growth of the microorganism, and, thus, enhance the effectiveness of the transformation process.

Upon completion of the transformation process, as evidenced by thin layer chromatography using silica gel plates (E. Merck, Darmstadt) and a solvent system consisting of 2:3 (by volume) ethyl acetate-cyclohexane, the desired transformed steroids are recovered by means well known in the art. For example, the fermentation (transformation) reaction mixture, including the fermentation liquor and cells, can be extracted with a water-immiscible organic solvent for steroids. Suitable solvents are dichloromethane (preferred), methylene chloride, chloroform, carbon tetrachloride, ethylene chloride, trichloroethylene, ether, amyl acetate, benzene and the like.

Alternatively, the fermentation liquor and cells can be first separated by conventional methods, e.g., filtration or centrifugation, and then separately extracted with suitable solvents. The cells can be extracted with either water-miscible or water-immiscible solvents. The fermentation liquor, freed of cells, can be extracted with water-immiscible solvents.

The extracts can be filtered through diatomaceous earth and the filtrate vacuum distilled to dryness. The resulting residue containing the desired transformed steroids then can be dissolved in a minimum of ethyl acetate-cyclohexane (20:80). This solution then can be chromatographed on dry silica gel using the solvent system ethyl acetate-benzene (20:80). ADD and AD can be separated from the silica gel by elution with the solvent system ethyl acetate-chloroform (15:85). The compounds then can be isolated as separate entities by evaporation of the solvent and recrystallization from hexane.

The desired products of the subject invention transformation process are the known steroid intermediates ADD and AD. These compounds are useful as intermediates in the synthesis of useful steroidal hormones. For example, ADD can be used to make estrone according to the process disclosed in U.S. Pat. No. 3,274,183. Also, AD can be used to make testosterone according to processes disclosed in U.S. Pat. Nos. 2,143,453; 2,253,798; 2,264,888 and 2,356,154.

The following examples are illustrative of the process and products of the subject invention but are not to be construed as limiting. All percentages are by weight and all solvent mixture proportions are by volume unless otherwise noted.

EXAMPLE 1

Preparation of Mutant *M. fortuitum* NRRL B-8153 from *M. fortuitum* ATCC 6842

(a) *Nitrosoguanidine Mutagenesis*

Cells of *M. fortuitum* ATCC 6842 are grown at 28° C. in the following sterile seed medium:

| | |
|---|---|
| Nutrient Broth (Difco) | 8 g/liter |
| Yeast Broth | 1 g/liter |
| Glycerol | 5 g/liter |
| Distilled Water, q.s. | 1 liter |

The pH is adjusted to 7.0 with 1 N NaOH prior to sterilization at 121° C. for 20 minutes.

The cells are grown to a density of about $5 \times 10^8$ per ml, pelleted by centrifugation, and then washed with an equal volume of sterile 0.1 M sodium citrate, pH 5.6. Washed cells are resuspended in the same volume of citrate buffer, a sample removed for titering (cell count), and nitrosoguanidine added to a final concentration of 50 μg/ml. The cell suspension is incubated at 37° C. in a water bath for 30 minutes, after which a sample is again removed for titering and the remainder centrifuged down and washed with an equal volume of sterile 0.1 M potassium phosphate, pH 7.0. Finally, the cells are resuspended in a sterile minimal salts medium, minus a carbon source, consisting of the following:

| | |
|---|---|
| NH$_4$NO$_3$ | 1.0 g/liter |
| K$_2$HPO$_4$ | 0.25 g/liter |
| MgSO$_4$ . 7H$_2$O | 0.25 g/liter |
| NaCl | 0.005 g/liter |
| FeSO$_4$ . 7H$_2$O | 0.001 g/liter |
| Distilled Water, q.s. | 1 liter |

The pH is adjusted to 7.0 with 1 N HCl prior to sterilization at 121° C. for 20 minutes. The cells are then plated out to select for mutants.

(b) Selection And Isolation Of Mutant *M. fortuitum* NRRL B-8153.

Mutagenized cells, as described above, are diluted and spread onto plates containing a medium consisting of the following (modified from Fraser and Jerrel. 1963. J. Biol. Chem. 205:291–295):

| Glycerol | 10.0 g/liter |
|---|---|
| $K_2HPO_4$ | 0.5 g/liter |
| $NH_4Cl$ | 1.0 g/liter |
| $MgSO_4 . 7H_2O$ | 0.5 g/liter |
| $FeCl_3 . 6H_2O$ | 0.05 g/liter |
| Distilled Water, q.s. | 1 liter |

Agar (15 g/liter) is added, and the medium is autoclaved at 121° C. for 30 minutes and then poured into sterile Petri plates.

Growth on this medium eliminates most nutritional auxotrophs produced by the mutagensis procedure, e.g. cultures that require vitamins, growth factors, etc. in order to grow on chemically defined medium are eliminated. After incubation at 28° C. for about 7 days, the resulting colonies are replicated to test plates suitable for selecting mutants and then back onto control plates containing the glycerol-based medium. The test plates are prepared as described by Peterson, G. E., H. L. Lewis and J. R. Davis. 1962. "Preparation of uniform dispersions of cholesterol and other water-insoluble carbon sources in agar media." J. Lipid Research 3:275–276. The minimal salts medium in these plates is as described above in section (a) of Example 1. Agar (15 g/liter), and an appropriate carbon source (1.0 g/liter), such as sitosterol or androstenedione (AD), are added and the resulting suspension autoclaved for 30 minutes at 121° C. The sterile, hot mixture is then poured into a sterile blender vessel, blended for several minutes, and then poured into sterile Petri plates. Foaming tends to be a problem in this procedure but can be reduced by blending when the mixture is hot and by flaming the surface of the molten agar plates. In this manner uniform dispersions of water-insoluble carbon sources are obtained which facilitates the preparation of very homogenous but opaque agar plates.

Colonies which grew on the control plates, but not on test plates containing AD as the sole carbon source, are purified by streaking onto nutrient agar plates. After growth at 28° C., individual clones are picked from the nutrient agar plates with sterile toothpicks and retested by inoculating grided plates containing AD as the carbon source. Purified isolates which still exhibit a phenotype different from the parental culture are then evaluated in shake flasks.

(c) Shake Flask Evaluation

Shake flasks (500 ml) contain 100 ml of biotransformation medium consisting of the following ingredients:

| $NH_4Cl$ | 3.0 g/liter | | |
|---|---|---|---|
| UREA | 0.5 g/liter | $CaCO_3$ | 3.0 g/liter |
| Cerelose | 10.0 g/liter | Tween 80* | 0.5 g/liter |
| $KH_2PO_4$ | 0.5 g/liter | Tap Water, q.s. | 1 liter |
| $MgSo_4 . 7H_2O$ | 0.5 g/liter | | |
| $FeCl_3 . 6H_2O$ | 0.5 g/liter | | |

*Atlas Refinery, Inc., Newark, New Jersey.

Soyflour (1 g/liter) is blended into the medium and then sitosterol (30 g/liter) is also blended into the medium. After the flasks are autoclaved for 30 minutes at 121° C., they are cooled to 28° C. and then inculated with 10 ml of seed growth prepared as follows:

The purified isolates from part (b) are grown on agar slants at 28° C. A loop of cells taken from a slant is used to inoculate a 500-ml flask containing 100 ml of sterile seed medium consisting of the following ingredients:

| Nutrient Broth (Difco) | 8 g/liter |
|---|---|
| Yeast Extract | 1 g/liter |
| Glycerol | 5 g/liter |
| Distilled Water, q.s. | 1 liter |

The pH is adjusted to 7.0 with 1 N NaOH prior to autoclaving the flasks at 121° C. for 20 minutes. The seed flasks are incubated at 28° C. for 72 hours.

As disclosed above, 10 ml of seed growth is then used to inoculate each 500-ml flask containing 100 ml of sterile transformation medium. The flasks are then incubated at 28° C. to 30° C. on a rotary shaker and sampled at various intervals. Ten ml samples are removed and extracted by shaking with 3 volumes of methylene chloride. Portions of the extracts are analyzed by thin layer chromatography using silica gel and the solvent system described above, i.e., 2:3 (by volume) ethyl acetatecyclohexane, and by gas-liquid chromatography. Evidence of the presence of ADD and AD confirms the selective degradation of sitosterol by the novel mutant produced from the parent *M. fortuitum* ATCC 6842.

EXAMPLE 2

Transformation of Sitosterol to ADD and AD

The medium used is the same as in Example 1 (c). This medium is sterilized by autoclaving 30 minutes at 121° C., whereupon it is cooled to 30° C. and then inoculated with 10 parts of a seed culture of the mutant mycobacterium *M. fortuitum* NRRL B-8153, prepared as described in Example 1(c). The inoculated mixture is incubated at 30° C. for 336 hours with agitation to promote submerged growth. Following incubation, the mixture is extracted with dichloromethane. The extract is dried over anhydrous sodium sulfate and the solvent is removed by vacuum distillation. The resulting residue is dissolved in a minimum of ethyl acetate-cyclohexane (20:80). This solution is then chromatographed on dry silica gel using the solvent system ethyl acetate-benzene (20:80). The presence of androst-4-ene-3,17-dione and androsta-1,4-diene-3,17-dione is shown by thin layer chromatography. These compounds are separated from the silica gel by elution with the solvent system ethyl acetate-chloroform (15:85). The compounds are then isolated by evaporation of the solvent and recrystallization from hexane.

EXAMPLE 3

By substituting *M. phlei* NRRL B-8154 for *M. fortuitum* NRRL B-8153 in Example 2, and an incubation temperature of 35° C. for 30° C., also in Example 2, there is obtained a mixture of ADD and AD.

EXAMPLE 4

By substituting cholesterol for sitosterol in Examples 2 and 3 there is obtained a mixture of ADD and AD.

EXAMPLE 5

By substituting stigmasterol in Examples 2 and 3 for sitosterol there is obtained a mixture of ADD and AD.

EXAMPLE 6

By substituting campesterol for sitosterol in Examples 2 and 3 there is obtained a mixture of ADD and AD.

EXAMPLE 7

By adding a combination of any of the steroids in Examples 2–6, in addition to sitosterol, or in place of sitosterol, in Examples 2 and 3 there is obtained a mixture of ADD and AD.

Example 8

By substituting a microorganism from the genera Arthrobacter, Bacillus, Brevibacterium, Corynebacterium, Microbacterium, Nocardia, Protaminobacter, Serratia, and Streptomyces, in Example 1 for *Mycobacterium fortuitum* ATCC 6842 and *Mycobacterium phlei* UC 3533, there are obtained mutant microorganisms which are characterized by their ability to selectively degrade steroids having 17-alkyl side chains of from 2 to 10 carbon atoms, inclusive, and accumulate ADD and AD in the fermentation beer.

EXAMPLE 9

By substituting the mutants obtained in Example 8 for *M. fortuitum* NRRL B-8153 and *M. phlei* NRRL B-8154 in Examples 2–7, there are obtained ADD and AD.

We claim:

1. A process, for preparing a mixture of androsta-1,4-diene-3,17-dione and androst-4-ene-3,17-dione which comprises cultivating *Mycobacterium fortuitum* NRRL B-8153 in an aqueous nutrient medium under aerobic conditions in the presence of a steroid containing from 2 to 10 carbon atoms, inclusive, in the 17-alkyl side chain, and recovering the produced androsta-1,4-diene-3,17-dione and androst-4-ene-3,17-dione.

2. A process, according to claim 1, wherein said steroid is sitosterol.

3. A process, according to claim 1, whererin said steroid is cholesterol.

4. A process, according to claim 1, wherein said steroid is stigmasterol.

5. A process, according to claim 1, wherein said steroid is campesterol.

6. A process for preparing a mixture of androsta-1,4-diene-3,17-dione and androst-4-ene-3,17-dione which comprises cultivating *Mycobacterium fortuitum* NRRL B-8153 in an aqueous nutrient medium under aerobic conditions in the presence of a mixture of two or more steriods wherein each steroid contains from 2 to 10 carbon atoms, inclusive, in the 17-alkyl chain, and recovering the produced androsta-1,4-diene-3,17-dione and androst-4-ene-3,17-dione.

7. A process, according to claim 6, wherein said steroid mixture is selected from the group consisting of sitosterol, cholesterol, stigmasterol, and campesterol.

8. A process for preparing a mixture of androsta-1,4-diene-3,17-dione and androst-4-ene-3,17-dione which comprises cultivating a mutant microorgansim of *Mycobacterium fortuitum*, said mutant being characterized by its ability to selectively degrade steroids having 17-alkyl side chains of from 2 to 10 carbon atoms, inclusive, and accumulate androsta-1,4-diene-3,17-dione and androst-4-ene-3,17-dione in the fermenation beer, in an aqueous nutrient medium under aerobic conditions in the presence of a steroid containing from 2 to 10 carbon atoms, inclusive, in the 17-alkyl side chain, and recovering the produced androsta-1,4-diene-3,17-dione and androst-4-ene-3,17-dione.

* * * * *